United States Patent [19]

Marcadet

[11] 4,224,319

[45] Sep. 23, 1980

[54] ANTISEPTIC COMPOSITION FOR TOPICAL APPLICATION TO THE SKIN

[76] Inventor: Ernest Marcadet, 9 rue Lakanal, Paris, France

[21] Appl. No.: 62,409

[22] Filed: Jul. 31, 1979

Related U.S. Application Data

[63] Continuation of Ser. No. 778,358, Mar. 17, 1977, abandoned, which is a continuation of Ser. No. 622,051, Nov. 14, 1975, abandoned, which is a continuation of Ser. No. 500,372, Aug. 26, 1974, abandoned, which is a continuation-in-part of Ser. No. 374,266, Jun. 27, 1973, abandoned.

[51] Int. Cl.$^2$ .................. A61K 31/56; A61K 31/355; A61K 31/195; A61K 31/07

[52] U.S. Cl. ................................ 424/238; 424/284; 424/319; 424/344

[58] Field of Search ............... 424/319, 238, 284, 344

[56] References Cited

U.S. PATENT DOCUMENTS

| | | | |
|---|---|---|---|
| 2,684,946 | 7/1954 | Schmitz | 424/319 |
| 2,700,683 | 1/1955 | Tesoro | 260/567.6 |
| 2,717,850 | 9/1955 | Schmitz | 424/319 |
| 2,865,859 | 12/1958 | Lubowe | 424/344 |
| 2,942,008 | 6/1960 | Lubowe | 424/344 |
| 2,968,628 | 1/1961 | Reed | 424/45 |
| 3,039,917 | 6/1962 | Schmitz | 424/319 |
| 3,574,850 | 4/1971 | Guillon | 424/319 |

FOREIGN PATENT DOCUMENTS 836956  6/1960  United Kingdom .

OTHER PUBLICATIONS

The Merck Index—8th Ed.—Merck & Co. Inc., (1968), p. 396.

*Primary Examiner*—Douglas W. Robinson
*Attorney, Agent, or Firm*—Norman S. Blodgett; Gerry A. Blodgett

[57] ABSTRACT

An antiseptic composition, particularly useful against bromidrosis, is prepared by using a disinfecting surface-active amino acid in water having dispersed therein one or several triglycerides of fatty acids of $C_{12}$ to $C_{20}$. The composition contains 0.3 to 5% by weight of the above bactericidal and fungicidal surface-active amino acid, a fatty material comprising said triglyceride, water and at least one of the vitamins A and E, and preferably also some sterols. The amino acid has the structure $RNH(R^1NH)_nR^2COOH$ where R is an aliphatic chain of 8 to 18C, $R^1$ and $R^2$ are $C_1$ to $C_3$ alkylenes, while n is 0 or 1.0 or 2.0. Preferably the composition further contains a pesticide quaternary ammonium derivative.

The composition is very effective agaist bromidrosis, particularly that of the feet, without any irritant action on the skin.

15 Claims, No Drawings

ANTISEPTIC COMPOSITION FOR TOPICAL APPLICATION TO THE SKIN

REFERENCE TO RELATED APPLICATION

This is a continuation, of application Ser. No. 778,358, filed Mar. 17, 1977, now abandoned, which is a continuation of application Ser. No. 622,051, filed Nov. 14, 1975, now abandoned, which is a continuation of application Ser. No. 500,372, filed Aug. 26, 1974, now abandoned, which is a continuation-in-part of application Ser. No. 374,266, filed June 27, 1973, now abandoned.

BACKGROUND OF THE INVENTION

The present invention relates to an antiseptic composition and more particularly a foam or cream for disinfecting the skin. It is especially useful against bromidrosis.

A large number of compositions for various disinfecting operatitons are known; when hygiene purposes are concerned, particularly the disinfection of regions of the skin where odours have a tendency to originate, the problem becomes rather difficult, because it is necessary to reconcile an efficient antiseptic effect with perfect harmlessness with respect to the skin. Now this result is often difficult to achieve, particularly where bromidrosis of the feet is concerned; it has in fact been found that, in the fight against the unpleasant and insalubrious effect, most of the known disinfecting agents are found to have an irritating effect or are even inefficient; on the other hand, given the complexity of the flora of the microorganisms which cause the bromidrosis, the action of the known antiseptic agents is generally incomplete and of short duration.

The present invention provides the solution to this delicate problem by the application of a new and very efficient composition, of which the action is lasting, because of the fixation of certain active agents on the skin, without any irritation being caused. Applicable to all kinds of hygienic care, the composition according to the invention is particularly effective in combating bromidrosis of the feet. While this composition may be liquid or creamy, its preferred form is a greasy foam which has very good cosmetic qualities in addition to its microbicidal and fungicidal activity.

The present invention results from the unexpected discovery that certain known ampholytic surface-active disinfectants, which in usual low concentrations have practically no effect on the bromidrosis, while at higher concentrations become irritant to the skin, can show extremely active at certain determined concentrations, and remain non-irritant, if special precautions are taken in accordance with the present invention.

It is known to employ, as disinfectants, amino acids with several amine functions, carrying at the end of their chain a heavy linear aliphatic radical, particularly a $C_8$ to $C_{18}$ alkyl, which have the advantage of not showing toxicity for human beings. Generally employed in concentrations of the order of 0.05 to 2% by weight, these agents act in an efficient manner against a large number of microorganisms, such as staphylococci, corynebacterium, coli, salmonella, pseudomona, etc. However, at concentrations exceeding about 0.3%, these amino acids become irritant to the skin, and this makes it necessary for the manufacturers thereof to block the amine functions ("Doprinate") or to decrease the number thereof; however, the activity against the bromidrosis is then considerably reduced. On the contrary, the amino acids in question, for instance, omega-N-alkyl-1-triaza-alkanoic acid, particularly "Dodicin" (The Merck Index, 1968, page 396) become very efficient against bromidrosis when they are used in concentrations higher than 0.3%, generally about 0.5 to about 5% by weight: unfortunately with these relatively strong concentrations, these agents have disadvantages as regards the skin.

In fact, this drawback has already been mentioned in 1958, in the British Pat. No. 836,956 on page 2, lines 7–10. The patent teaches that exceptionally n-dodecyl-1,3-propylenediamino-acetic acid hydrochloride, even in a 10% solution, does not cause any visible redness on the skin. However, while that is true with a "cloth-skin test" (page 2, lines 30–34 of the patent) which lasts a short time, the result is quite different when the above compound is repeatedly applied to human or animal skin: then, even an aqueous 0.3% solution of it produces irritation after some days.

Thus, all the amino-acids containing disinfectant compositions, described for example in U.S. Pat. Nos. 2,717,850 and 3,574,850 are harmful to skin when they have 0.3% or more amino-acid and are used repeatedly. Such compositions are suitable for disinfecting by a wash made once or from time to time, but cannot be left in contact with the skin for several hours or days.

The above drawback is undoubtedly the reason for which, in spite of the excellent disinfectant properties of amino-acids bearing a rather long aliphatic chain, these compounds have not been used until now in cosmetic or hygienic compositions designed for long time contact with the skin.

SUMMARY OF THE INVENTION

It is an object of the present invention to provide a new aqueous disinfectant composition the main active agent of which is an amino-acid of the above set forth kind, and which is harmless to the skin while exerting a strong pesticidal action on microorganisms which develop on the skin.

Another object of the invention is to provide a cream, ointment, or foam formed by an aqueous dispersion of one or several fatty substances, the water of the dispersion having dissolved therein one or several amino-acids carrying at the end of their chain a heavy linear aliphatic group.

A further object of the invention is the provision of a deodorant composition efficient against bromidrosis, which may remain in contact with the skin for long periods of time, without any damage to the skin.

According to the invention, the new composition contains an aqueous solution of one or several amino-acids represented by the formula:

$$R-NH-(R^1-NH)_a-R^2-COOH$$

wherein R is an aliphatic chain of 8 to 18 carbon atoms, $R^1$ and $R^2$, identical or different, are $C_1$ to $C_3$ alkylenes, while n is 0 or 1, or 2; the amount of the amino-acids is of 0.3 to 5% by weight of the composition, and the composition must contain dispersed therein 1.5 to 15% by weight of one or several triglycerides of fatty acids having 12 to 20 carbon atoms, and at least one of the vitamins A and E, at a concentration of 0.015 to 15 milligrams (50 to 50,000 International Units) per 100 grams of composition as concerns vitamin A, and 0.5 to 50 milligrams (0.55 to 55 Internat. Units) in 100 grams of composition as concerns vitamin E.

While various other materials may also be advantageously present in the composition, the essential feature of the invention is the use of the indispensable main three sorts of substances: amino-acid, triglyceride of fatty acid and at least one of the vitamins A and E, as above pointed out. That is the condition of obtaining good disinfecting effect and no irritation to the skin.

DESCRIPTION OF THE INVENTION

Among the tensioactive amino-acids of the above formula certain are easily available in commerce; here is a non limitative list of some of them.

TABLE 1

| Formula | Commercial name or trademark and name of producers. |
|---|---|
| A. $RNHCH_2CH_2COOH$ | AMPHORAM (Societe Pierrefitte-Auby) |
| B. $RNH(CH_2)_3NH(CH_2)_2COOH$ | DIAMPHORAM (Societe Pierrefitte-Auby) |
| C. $RNH(CH_2)_2NH(CH_2)_2NHCH_2COOH$ | LODICIN (Th.Goldschmidt Company) |
| D. $RNH(CH_2)_3NH-CH-CH_2COOH$<br>           $\quad\quad\quad\quad\quad\quad\quad\ \|$<br>           $\quad\quad\quad\quad\quad\quad\ CH_3$ | TEGOLAM (Th.Goldschmidt Company) |
| E. $R[NH(CH_2)_3]_2NH(CH_2)_2COOH$ | TRIAMPHORAM (Societe Pierrefitte-Auby) |

The commercial products are mixtures of compounds of various R having 8 to 18 carbon atoms; that means it is a mixture of compounds the R group of which is mainly octyl, capryl, lauryl, myristyl, cetyl, stearyl, oleyl and linoleyl, while the $C_{12}$ and $C_{18}$ groups are generally dominant.

Other usable amino-acids are for example: n-dodecyl-aminoacetic acid, n-tetradecyl-amino-propionic acid, n-hexadecyl-aminoacetic acid, hexadecyl-aminobutyric acid, stearyl-aminoacetic acid, stearyl-aminopropionic acid, oleyl-aminoacetic acid, oleyl-aminopropionic acid, linoleyl-aminoacetic acid, linoleyl-aminobutyric acid, dodecyl-ethylenediamino acetic acid, dodecyl-ethylenediamino-propionic acid, dodecyl-diethylene-triamino-propionic acid, oleyl-ethylene diamino-acetic acid, stearyl-ethylene diamino-propionic acid, linoleyl-ethylene-diamino butyric acid, linoleyl-diethylene-triamino-propionic acid etc. This list being by no means limitative.

Particularly suitable amino-acids are those in which n=2, that means the number of amine functions is 3, while $R^1$ is $-CH_2CH_2-$ or $-CH_2CH_2CH_2-$, $R^2$ being $-CH_2-$, $-CH_2CH_2-$ or

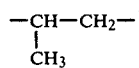

The toxicity of such compounds, determined in male and female rats leds to values of $LD_{50}$ of 5,000 to 11,000 mg/kg of animal per os.

The preferred concentration of amino-acid in the composition is about 0.5 to 2% by weight.

The triglyceride or triglycerides, which are necessary in the composition according to the invention, are glycerol triesters of the fatty acids in $C_{12}$ to $C_{20}$, which acids include saturated and non saturated ones, and may bear an hydroxy group in their molecule. It is of course most convenient to use glycerides of the fatty acids which are available in vegetal or animal products, i.e. oils and fats. Thus, the most current acids are: lauric (dodecanoic), myristic (tetradecanoic), palmitic (hexadecanoic), stearic (octadecanoic), arachidic (eicosanoic), palmitolic (hexadecenoic), oleic (octadecenoic), eleostearic (octadecatrienoic), linoleic (octadecadienoic), linolenic (octadecatrienoic), arachidonic (eicosatetraenoic), ricinoleic (hydroxy-octadecenoic).

The above fatty acids exist in natural oils and fats, in the form of glycerides, and can be exerted therefrom. Oils and fats which contain sufficiently pure triglycerides may be used themselves for the purpose of the present invention. Thus, for example, the following materials may be used, the approximate content of which in fatty acids is quoted in the following table 2.

TABLE 2

|  | Almond oil | Olive oil | Corn oil | Tallow |
|---|---|---|---|---|
| Fatty acids % |  |  |  |  |
| oleic | 77 | 80 | 46 | 48 |
| linoleic | 17 | 7 | 42 | 3 |
| palmitic | 4 | 10 | 8 | 33 |
| myristic | 1 |  |  |  |
| stearic |  | 1 | 3 | 15 |
| arachidic |  | 1 |  |  |

The natural oils and fats may be used provided they do not contain irritant substances such as certain free acids, oxidization products, aldehydes eventually formed during heating, etc. For this reason cold expressed and adequately purified oils are preferable. On the other hand it is important that the free acid number of the fatty material does not exceed 3 and be preferably less than 1.

According to the invention the composition must contain a certain amount of vitamin A, that means of 3,7-dimethyl-9(2,6, 6-trimethyl-1cyclohexen-1-yl)-2,4,6,8-nonatetraen-1-ol, or of vitamin E i.e. tocopherol. If none of these substances is present the application of the composition on the skin produces redness or eruption with less or more inflammation, after a few days of contact. There is yet irritation when the composition contains less than 50 Intern. Units % of vitamin A, or less than 0.75 I.U. of tocopherol (vitamine E). Best results are obtained with such dosages as 1,000 to 5,000 I.U. vitamin A or 1 to 25 I.U. vit. E. Higher doses are not useful, as harmlessness to skin, obtained with 5,000 I.U.% vitamin A scarcely improves when the dose reaches 50,000 I.U.%, and does not change at all above the 50,000 I.U.%. Similarly few is gained in increasing the tocopherol content up to 55 I.U.% and nothing above this figure.

Preferably both vitamins A and E are added to the composition of the invention; it contributes to avoid individual sensitiveness of the skin of certain person; in fact there are cases where the vitamin A has better action than E and other cases where, on the contrary, E is more efficient.

According to a further feature of the invention, it is advantageous that some sterols be present in the composition. Their presence improves the behaviour of the composition relatively to the skin. The sterols used may be such as cholesterol, agnosterol, ergosterol, (vitamin D), dehydrocholesterol, cholestanol, beta-sitosterol, zymosterol, lathosterol, hydroxycholesterol, dehydroergosterol, ascosterol and/or other sterols of phytosterols which can be obtained from natural products or by synthesis.

Although the vitamins and the sterols can be individually incorporated into the excipient of the new composition, they can also be taken in the form of a fatty substance which normally contains them in sufficient quantity. This is particularly the case with certain first-pressing, pure vegetable oils, as for example olive oil, palm oil, hazel nut oil and especially sweet almond oil, which contain sterols and the vitamins, particularly E and A.

On the other hand, sterols, particularly ergosterol, viosterol or calciferol (vitamins D) can be supplied by certain animal fats, such as lanolin. The proportion of vitamins D can vary widely from a very small quantity of a few units up to millions of units per 100 g of composition. preferably, there are used 50 to 50,000 units of them. As regards the various other sterols, their proportion can also vary within wide limits, but it is preferably from 0.02 to 0.5% by weight of the whole composition.

The composition can be presented in the form of an emulsion, ointment, lotion or foam, prepared in known manner with appropriate ingredients which are harmless to the skin. It is generally to be recommended that the fatty substance of the composition amounts to 2 to 10% by weight, water 50 to 85% or better still 70 to 80%, while the composition may contain in addition other suitable adjuvants at the rate of about 1 to 10%.

The composition according to the invention may be constituted only of the tensio-active amino-acids, the fatty substance (triglyceride) and vitamins A or/and E, and preferably also sterols. However in order to impart to the composition required physical properties and good cosmetical qualities, it is generally advantageous to include therein various other materials. Thus, where a foam is concerned, the addition of higher alcohols, polyalcohols and wetting agents such as alkanolamines, etc. is useful. Hence, an excellent greasiness and fineness can be imparted to the composition by the addition of cetyl alcohol, especially when it is used concurrently with lanolin. Likewise, glycerine, propylene glycol or other glycols are useful for permitting a good spreading and penetration of the composition into the skin.

Among the alkanolamines, it is possible in particular to choose triethanolamine, the purpose of which is known in cosmetic compositions.

It should be noted that the composition according to the invention provides the protection of the skin against microorganisms by penetration into the skin, and not by the formation of a surface film, as in the case with silicones or other filmogenic agents so far used.

The disinfecting, surface-active amino-acid or acids being used according to the invention in relatively high concentrations generally act at the same time as a bactericide and as a fungicide; however, for broadening the spectrum of the antiseptic action of these agents, it may be useful to add to them a small proportion of one or of several additional bactericides and/or fungicides, or even bacteriostatic and/or fungistatic agents. These adjuvants can be taken from the different classes of known active compounds, for example, from phenol antiseptics and antibiotics. A very small dose of the additional agent is generally sufficient for obtaining an improved fungistatic effect and a more powerful bactericidal action. In general, the additional pesticidal (or bacteriostatic or fongistatic) agent is only used at the rate of about 1/200 to ¼ of the quantity of the disinfecting, surface-active amino acid.

Particularly useful additional agents are quaternary ammonium derivatives which possess pesticidal properties. More especially useful such compounds are those of the structure

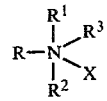

where $R^1$ and $R^2$ are lower alkyls, R is a heavy $C_8$ to $C_{20}$ alkyl and preferably $C_{12}$ to $C_{18}$, $R^3$ being an alkyl group which may bear an aryl radical, while X is a monovalent anion, for example chlorine, bromine, acetate, propionate, tartarate, phosphate, saccharinate etc. Compounds of this kind are well known in the art and described in numerous patents and other publications (U.S. Pat. Nos. 2,691,676; 2,700,683; 2,676,986; 2,547,365 etc.), then it is not necessary to further describe them here.

Non limitative examples of quaternary ammonium derivatives, suitable to the working of the present invention, are compounds of the above formula wherein R is a $C_{12}$ to $C_{18}$ alkyl, $R^1$ and $R^2$ are methyls, ethyls or propyls, $R^3$ being a benzyl group or a grouping $—(CH_2)_n$ COOH in which n is an integer of 1 to 8. Among these compounds are aryl-dimethyl-benzyl-ammonium chlorides and bromides and saccharinates, particularly lauryl-dimethyl-benzyl-ammonium saccharinate and other similar derivatives. Can also be used such compounds as the salts of benzyl-dimethyl-2-hydroxycyclooctyl-ammonium or corresponding piperidinium salts, as well as a salt of para-alkyl-benzyl-triethylammonium the alkyl of which has 12 to 18 carbon atoms.

The quaternary ammonium compounds the anion of which is derived from an organic acid having no halogen in its molecule are preferred; thus acetates, tartrates, propionates, salicylates and particularly saccharinates are better than chlorides or bromides because they are less toxic.

Inasmuch as the amino-acids used, and even the quaternary ammonium salts, can exhibit somewhat basic reaction, care should be taken that the composition prepared with them have not an excessive alkalinity which could produce irritation on the skin, in spite of the addition of triglyceride and vitamin A or/and E. Then, when the starting materials of the composition are of basic nature, they or the finished composition should be neutralized with a non irritant acid, in order that the pH of the composition be comprised in the range of 5.5 to 8, and preferably 6 to 7.5. For this purpose such acids may be used as, for example, acetic, benzoic, boric, caproic, caprylic, citric, lactic, methoxybenzoic, phosphoric, saccharinic, salicylic, tartric, oleic, stearic and the like.

As known, certain ointments for dermatitis therapeutics are relatively acid, their pH being about 5.5; then a moderate acidity of the compositions according to the invention can be useful in certain cases of dermatitis, and their pH may be adjusted to about 5.5–6.5. However in most of the applications of the invention it is preferable that the pH of the composition is about 6 to 7.5 and yet better 6.5 to 7.2.

PREPARATION OF THE COMPOSITION

The following examples illustrate the preparation of some non limitatively formulated disinfecting compositions according to the invention.

EXAMPLE 1

Three grams of a commercial solution of 65% alkyl-aminopropionic acid R—NH—CH$_2$CH$_2$COOH in isopropanol (R being C$_8$ to C$_{18}$ with about 60% C$_{12}$), that means 1.95 g of amino-acid, are dispersed in 100 ml of water and neutralized to pH7 with triethanolamine. To the viscous and very tensioactive solution obtained 6 g of oleic triglyceride

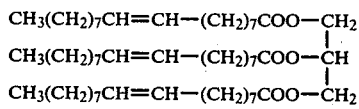

are added together with 2,000 I.U. of vitamin A (0.6 mg axerophtol taken in the form of palmitate), and the mixture is thoroughly homogenized.

The emulsion thus obtained constitutes a good disinfecting composition which may be used for washing infected regions of the skin as well as a permanent deodorant.

EXAMPLE 2

The preparation of example 1 is repeated except that the water is also added with 0.3 g of lauryl-dimethyl-benzyl-ammonium bromide. The disinfecting effect obtained is stronger than that which would be expected by additivity of the effects of the components used.

EXAMPLE 3

In the procedure of example 1 the amino-acid is replaced by 1.6 g of lauryl-ethylene-diamino-acetic acid C$_{12}$H$_{25}$—NH—CH$_2$CH$_2$—NH—CH$_2$COOH which has not to be neutralized. Instead of oleic triglyceride 5 g of olive oil are dispersed in the aqueous solution of the amino-acid, together with 9 mg of d-α-tocopherol taken in the form of its acetate (6.05 I.U. vitamin E). The emulsion obtained shows disinfecting properties equivalent to those of example 1.

EXAMPLE 4

0.9 g of stearyl-propylene-diamino-propionic acid are dissolved in 100 ml of water; 2.5 g of linoleic triglyceride, 400 I.U. of vitamin A and 30 mg of ergosterol are added to the solution and the mixture is thorougly homogenized.

EXAMPLE 5

The water of example 4 is added with 0.19 g of stearyl-dimethyl-benzyl-ammonium chloride, whereby altogether the dispersing power of the solution and its disinfecting effect are enhanced.

EXAMPLE 6

A commercial solution of alkyl-dipropylene-triamino propionic acid R(NHCH$_2$CH$_2$CH$_2$)$_2$NHCH$_2$CH$_2$COOH (R=C$_8$ to C$_{18}$ with 56% C$_{12}$ and 18% C$_{14}$) in isopropanol and water is used for the preparation of an aqueous solution having 3.2% by weight of the amino-acid.

As the solution is basic, it is neutralized to pH 7.6 with acetic acid.

4 g of ricinoleic triglyceride and 3 g of stearic triglyceride are added to 100 g of the solution together with 1,000 I.U. of vitamin A and 2 I.U. of vitamin E.

EXAMPLE 7

A composition similar to that of example 6 is prepared with the addition of 0.26 g of lauryl-dimethyl-benzyl-ammonium saccharinate. Its disinfecting activity is increased more than it would be expected with the amount of saccharinate added.

EXAMPLE 8

An aqueous emulsion is prepared with the following ingredients the amounts of which are expressed in percents by weight:

| | |
|---|---|
| n-dodecyl-propylene-diamino-acetic acid C$_{12}$H$_{25}$—NHCH$_2$CH$_2$CH$_2$NHCH$_2$COOH | 1.0 |
| n-dodecyl-dimethyl-benzyl-ammonium saccharinate | 0.2 |
| lauryl alcohol (dodecanol) | 0.5 |
| purified lanoline (containing about 16% of sterols among which 2.9% ergosterol) | 0.5 |
| propylene glycol Codex | 4.0 |
| tocopherols (vitamin E) 1 mg per 100 g | |
| vitamin A 4,000 I.U. | |
| calciferol (vitamin D) 800 I.U. | |
| butyl oleate | 1.0 |
| parfume | 0.5 |
| distilled water : balance to 100 g | |

In the course of the preparation the pH of the emulsion is brought to 6.6 by adding an aqueous 15% solution of citric acid.

The emulsion perfectly deodorizes various regions of the body, particularly the feet, without any irritation. The presence of lanoline, lauryl alcohol, and propylene-glycol improves the cosmetic qualities of the product, that means its spreading, adhering and penetrating in the skin.

EXAMPLE 9

A foam is prepared using the following aqueous emulsion (% by weight):

| | |
|---|---|
| oleyl-diamino-propylene-isobutyric acid C$_{18}$H$_{35}$—NH—CH$_2$CH$_2$CH$_2$—NH—CH(CH$_3$)—CH$_2$—COOH | 1.6 |
| stearyl-dimethyl-benzyl-ammonium chloride | 0.4 |
| cetyl alcohol | 1.1 |
| stearic acid | 1.5 |
| lanoline (same as in example 8) | 0.6 |
| glycerine Codex | 4.0 |

-continued

| | |
|---|---|
| palm oil | 2.5 |
| tocopherols (vitamin A) | 1.1 mg per 100 |
| vitamin A | 3,000 I.U. |
| calciferol (vitamin D) | 500 I.U. |
| triethanolamine | 0.9 |
| parfume | 0.5 |
| distilled water | balance to 100 |

No neutralization is necessary in view of the equlibrated proportions of acidic and basic components present. 12% of "propellant 21" (dichlorofluoromethane) are added as propellant of the foam, and the mixture is conditioned in appropriate cans.

EXAMPLE 10

A foam is prepared according to the following formulation calculated for 100 g of composition.

| | |
|---|---|
| linoleyl-diamino-propylene-propionic acid $C_{18}H_{33}$—$NHCH_2CH_2CH_2NHCH_2CH_2COOH$ | 4.7 |
| myristyl-dimethyl-benzyl-ammonium saccharinate | 0.17 |
| octyl alcohol | 0.8 |
| linoleic acid | 1.0 |
| lanoline (same as in example 8) | 2.0 |
| almond oil (sweet, described after example 14) (vitamin A 3,000 I.U., vitamin E 20 I.U., vitamin D 700 I.U. contained in the almond oil) | 5.0 |
| triethanolamine | 1.1 |
| parfume | 0.4 |
| distilled water : balance to 100 | |

14 g of "propellant 21" (dichlorofluoromethane) are used and the foam is stored in sprays, particularly useful for deodorizing armpils.

EXAMPLE 11

A less stronger deodorant, particularly for children, is made as in example 10 but the amount of the amino-acid is reduced to 0.6%, and consequently that of lanoline to 0.4% and that of almond oil to 2.5%.

EXAMPLE 12

In example 9 the stearyl-dimethyl-benzyl-ammonium chloride is replaced by 0.3% of "Hyamine" i.e. p-tert-octyl-phenoxyethyl-phenoxyethyl-dimethyl-ammonium chloride.

EXAMPLE 13

A foam, particularly useful against bromidrosis, has the following % composition:

| | |
|---|---|
| dodecyl-triamino-diethylene-acetic acid $C_{12}H_{25}$—$NH$—$CH_2CH_2$—$NH$—$CH_2CH_2$—$NHCH_2COOH$ | 1.40 |
| 2,4,4'-trichloro-2'-hydroxy-diphenylether | 0.08 |
| cetyl alcohol | 0.80 |
| stearic acid | 1.60 |
| purified lanoline (same as in example 8) | 0.40 |
| propylene glycol Codex | 4.00 |
| sweet almond oil Codex 1949 (described below; containing sterols and vitamins A and E) | 2.50 |
| Vitamin A 3,000 I.U. <br> Vitamin E 20 I.U.   in the almond oil <br> Vitamin D 700 I.U. | |
| triethanolamine | 1.10 |
| parfumes | 0.52 |
| distilled water: balance to 100 | |

100 g of the mixture are added with 14 g of "propellant 21" and charged into sprays.

EXAMPLE 14

In the foam of example 13, the additional antiseptic (trichloro-hydroxy-diphenylether) is replaced with 0.2% of alkyl-dimethyl-benzyl ammonium saccharinate the alkyl of which comprises 50% $C_{14}$, 40% $C_{12}$ and 10% $C_{16}$ (sold by ONYX Chemical Company under the trade-mark "Onyxide 3300"). Harmlessness to skin is thus yet improved and any toxicity avoided.

The sweet almond oil, employed in the above compositions, is a virgin pure oil, derived from Amygdalus seeds by first pressing and in the cold; it thus contains all its active compounds, especially sterols and vitamins E and A. It thus participates in the cutaneous transport of the active elements, while also playing an important protective role. Its indices are: saponification 189–195, iodine 92–103, peroxides (mcg $O_2$/g of oil) lower than 200; free acidity lower than 0.35; oleic acid 75%, linoleic acid 15%, unsaponifiable acids 0.1%.

The lanolin used has the numbers: saponification 91–106, iodine 18–32, acid 0.2–0.5. It contains 45 to 54% of unsaponifiable substances, of which the main constituents are: cholesterol-agnosterol and cetyl, ceryl, lanooctadecyl alcohols. It contains ergosterol, the origin of vitamin D, providing an anti-inflammatory effect.

The foams of examples 13 and 14 were tested each by 10 persons particularly subject to bromidrosis of the feet: during the summer, with an outside temperature ranging between 17° and 26° C., on average one single application per week was sufficient for eliminating all septic manifestation. None of the 20 persons experienced any irritation of the skin of the feet after six weeks of application of the foam.

Before these tests, 10 of the above persons used one of the best commercial deodorants; 8 of them must apply the product every 2 days, as after 2 days bromidrosis became perceptible.

Similar tests were made (1) with aerosols of examples 13 and 14 containing only 0.5% by weight of the amino-acid instead of 1.4%, and (2) with aerosols having each a content of 2.8% of the amino-acid. Then the above reported results were obtained with (1) only when outside temperature was in the range of 10° to 17° C., while the compositions (2) lead to the same results even during a rather hot period with 30° to 40° C. outside temperatures.

TESTING THE IRRITATION OF SKIN

Tests have been carried out on mice, which consisted in applying onto an area of about 1 sq. cm. of the animals abdomen a thin layer of one of the solutions or emulsions specified in the following table 3. The application was repeated on 3 animals with each reagent, every day until redness, pimple, pustule or other sign of irritation appeared. In table 3 under heading "Days" the average time for 3 animals is quoted. the concentration are % by weight of amino-acid in water. When triglyceries are involved, it is understood they are in the form of emulsion in the aqueous solution of amino-acid. Also vitamin A is dispersed in that solution; it is dissolved in triglyceride when this is present.

inoculated with a smear taken from between toes of a person suffering of strong bromidrosis. The Petri dishes

TABLE 3

| Composition | Concentration % in amino-acid | Days |
|---|---|---|
| Control: pure water | 0 | 120 |
| Amino-acid "C" of Table 1 | 0.1 | 40 |
| Amino-acid "C" of Table 1 | 0.2 | 17 |
| Amino-acid "C" of Table 1 | 0.3 | 10 |
| Amino-acid "C" of Table 1 | 0.5 | 7 |
| Amino-acid "C" of Table 1 | 1.0 | 4 |
| Amino-acid "C" of Table 1 | 3.0 | 2 |
| Amino-acid "C" + 1 I.U. % vitamin E | 1.0 | 6 |
| "C" + 400 I.U. % vitamin A | 1.0 | 8 |
| "C" + 3% pure oleic triglyceride | 1.0 | 6 |
| "C" + 3% pure oleic triglyceride + 40 I.U. % vitamine A | 1.0 | 6 |
| "C" + 3% pure oleic triglyceride + 400 I.U. % vitamine A | 1.0 | 28 |
| "C" + 3% pure oleic triglyceride + 4,000 I.U. % vitamine A | 1.0 | 63 |
| "C" + 0.5. lanoline free from vitamins A and E | 1.0 | 9 |
| "C" + 3% sweet almond oil | 1.0 | 10 |
| "C" + 3% sweet almond oil + 0.5% lanoline + 1 unit vitamin E | 1.0 | 29 |
| "C" + 3% sweet almond oil + 4,000 I.U. vitamine A | 1.0 | 63 |
| "C" + 3% pure oleic triglyceride + 0.1 I.U. vitamin E | 1.0 | 7 |
| "C" + 3% pure oleic triglyceride + 1 I.U. vitamin E | 1.0 | 25 |
| "C" + 3% pure oleic triglyceride + 10 I.U. vitamin E | 1.0 | 69 |
| "C" + 3% sweet almond oil derived from vitamins A and E + 0.6% ergosterol | 1.0 | 10 |
| "C" +3% sweet almond oil derived + 12,000 I.U. vitamine A from vitamins A and E + 40 I.U. vitamine E | 1.0 | 82 |
| Composition of example 13 | | 96 |
| Amino-acid "A" of Table 1 | 0.1 | 22 |
| (R being linoleyl) | 0.3 | 6 |
| | 1.0 | 2 |
| Amino-acid "A" of Table 1 (R being linoleyl) Amino-acid "A" of Table 1 + 4% lauric triglyceride (R being linoleyl) + 5,000 I.U. vitamine A | 1.0 | 68 |
| Amino-acid "B" of Table 1 (R being palmityl) | 0.1 | 31 |
| | 1.0 | 4 |
| | 2.0 | 2 |
| Amino-acid "B" of Table 1 + 5% ricinoleic triglyceride (R being palmityl) + 22 I.U. vitamin E | 2.0 | 71 |
| Amino-acid "D" of Table 1 formed by a mixture of acids the R of which in olelyl and linoleyl | 0.1 | 29 |
| | 3.0 | 3 |
| Amino-acid "D" of Table 1 + 6% myristic triglyceride formed by a mixture of acids + 500 I.U. vitamin A the R of which is oleyl and linoleyl + 15 I.U. vitamin E | 3.0 | 67 |

From Table 3 one can see that taken alone or with either vitamins (A or/and E) or triglycerides, the amino-acids at more than 0.3% produce irritation in 2 to 10 days. When all the three products are used together (amino-acid+vitamin+triglyceride) no irritation occurs before 63 to 96 days.

TESTING DISINFECTING ACTIVITY

A nutritive broth is prepared by dissolving 10 g of peptone, 10 g of glucose, 2 g NaCl, 0.5 g $MgSO_4.7H_2O$ and 26 g of gelose in 1,000 ml water. The solution is heated to 100° C. and poured in sterile conditions into Petri dishes. After cooling and solidifying, the gelose is inoculated with a smear taken from between toes of a person suffering of strong bromidrosis. The Petri dishes are then kept at 35° C. until the characteristic nasty odour of bromidrosis develops.

The thus obtained culture is used as seed for the inoculation of the same gelose broth in a series of Petri dishes, in which various substances are spread on the surface of the gelose. All the dishes are now kept at 35° C. and for each of them the time is noted after which the gelose evolves a nasty odour.

In the following Table 4 under heading "Disinfectant" is specified the nature of aqueous compositions spread on the gelose; the heading "Time" indicates the number of days after which the odour became sharply perceptible.

TABLE 4

| Culture N | Disinfectant | Time (days) |
|---|---|---|
| 1 | Control (distilled water) | 1½ |

TABLE 4-continued

| Culture N | Disinfectant | Time (days) |
|---|---|---|
| 2 | 0.2% solution lauryl-dimethyl-benzyl-ammonium chloride | 2⅔ |
| 2a | 1% solution lauryl-dimethyl-benzyl-ammonium chloride | 6 |
| 3 | 0.2% lauryl-dimethyl-benzyl-ammonium saccharinate | 2½ |
| 3a | 1% lauryl-dimethyl-benzyl-ammonium saccharinate | 6 |
| 4 | 0.05% soln 2,4,4'-trichloro-2'-hydroxy-diphenylether | 3½ |
| 5 | 0.1% amino-acid "C" of Table 1 | 2 |
| 5a | 0.3% amino-acid "C" of Table 1 | 8 |
| 5b | 1.0% amino-acid "C" of Table 1 | 27 |
| 6 | 0.1% amino-acid "A" of Table 1 | 2 |
| 6a | 1.0% amino-acid "A" of Table 1 | 25 |
| 7 | 1.0% amino-acid "A" of Table 1 +0.2% quatern. ammon. n°2 above | 35 |
| 7a | 1.0% amino-acid "C" of Table 1 +0.2% quatern. ammon. n°3 above | |
| 7b | 1.0% amino-acid "C" of Table 1 (solution 7a) + 3% oleic triglyceride | 37 |
| 8 | 0.1% amino-acid "B" of Table 1 | 2½ |
| 8a | 1.0% amino-acid "B" of Table 1 | 24 |
| 8b | 1.0% amino-acid "B" of Table 1 + 0.2% stearyl-dimethyl-benzyl-ammonium bromide | 33 |
| 8c | 1.0% amino-acid "B" of Table 1 (solution 8b) +3,5% palm oil | 35 |

It results from the cultures of Table 4 that low concentrations of amino acids (no. 5, 6, 8) have weak disinfecting action on bromidrosis, while the action becomes very strong with about 1% of these acids (nos. 5b, 6a, 8a). On the other hand, quaternary ammonium known antiseptics at a concentration of 1% (nos. 2a, 3a) exert an action much less than 1% solutions of amino-acids do, and even less than a 0.3% solution (no. 5a) of those acids. An interesting fact is that the joint use of amino-acids and quaternary ammonium compounds produces a synergistic effect (nos. 7, 7a, 7b, 8a, 8b) the action of their mixtures being stronger than the sum of the actions of each of the components.

Cultures no. 7b and 8c show another unexpected fact: the action of a mixture of amino-acid and quaternary ammonium when added with a triglyceride is stronger than without the fatty substance. This fact is quite surprising in view of the teaching of U.S. Pat. No. 2,717,850 (col.4, lines 25–27), U.S. Pat. No. 3,039,917 (col.2, lines 58–61) and British Pat. No. 836,956 (page 5, lines 39–42), according to which fatty substances may reduce the disinfecting power of tensioactive amino-acids. Now, one must conclude teachings of prior art do not apply to deodorants and particularly to anti-bromidrosis compositions.

I claim:

1. An aqueous composition, for prolonged application to the skin without irritation and useful against bromidrosis, which comprises an aqueous solution of a surface-active amino-acid having the structure

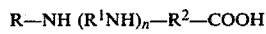

where R is an aliphatic chain of 8 to 18 carbon atoms, $R^1$ and $R^2$, identical or different, are $C_1$ to $C_3$ alkylenes, while n is 0 to 1, the amount of the amino-acid being of 0.3% to 5% by weight of the composition, and the solution contains dispersed therein 1.5% to 15% by weight of a triglyceride of a fatty acid having 12 to 20 carbon atoms, and at least one of the vitamins A and E at a concentration of 40–12,000 International Units per 100 grams of composition as concerns the vitamin A and 1.0–40 International Units per 100 grams of composition as concerns vitamin E.

2. The composition according to claim 1, wherein the content of vitamin A is of 1,000 to 5,000 I.U. per 100 grams of composition.

3. The composition according to claim 1, wherein the content of vitamin E is 1 to 25 I.U. per 100 grams of composition.

4. The composition according to claim 1, which contains one or more sterol selected from the group consisting of cholesterol, agnosterol, ergosterol, dehydrocholesterol, cholestanol, beta-sitosterol, zymosterol, lathosterol, hydroxycholesterol, dehydro-ergosterol, and ascosterol in an amount of 0.02 to 0.5% by weight of the composition.

5. The composition according to claim 1, wherein said amino-acid is selected from the group consisting of n-dodecyl-aminoacetic acid, n-tetradecyl-amino-propionic acid, n-hexadecyl-aminoacetic acid, hexadecyl-aminobutyric acid, stearyl-aminoacetic acid, stearyl-aminopropionic acid, oleyl-aminoacetic acid, oleyl-aminopropionic acid, linoleyl-aminoacetic acid, linoleyl-aminobutyric acid, dodecyl-ethylenediamino acetic acid, dodecyl-ethylenediamino-propionic acid, dodecyl-diethylenetriamino-propionic acid, oleyl-ethylene diamino-acetic acid, stearyl-ethylene diamino-propionic acid, linoleyl-ethylene-diamino butyric acid, and linoleyl-diethylene-triamino-propionic acid.

6. The composition according to claim 1, where said amino-acid consists of a mixture of at least two amino-acids each having different aliphatic chains R in the range of $C_8$ to $C_{18}$.

7. The composition according to claim 1, wherein the said triglyceride is selected from the group consisting of olive oil, palm oil, hazel nut oil, and sweet almond oil.

8. The composition according to claim 1, which contains a quarternary ammonium pesticide of the formula

where R is a alkyl having 12 to 18 carbon atoms, $R^1$ and $R^2$ are lower alkyls, $R^3$ is a radical selected from the group consisting of lower alkyls and benzyl, and X is an anion selected from the group consisting of chloride, bromide, acetate, propionate, tartarate, phosphate and saccharinate, the amount of the ammonium pesticide being in the range of 1/200 to ¼ of the weight of the amino-acid.

9. The composition according to claim 1, the pH of which is in the range 5.5 to 8.

10. The composition according to claim 9, which has a pH value adjusted to a value in the range of 6 to 7.5.

11. The composition according to claim 1, which contains a sterol in an amount of 0.02 to 0.5% by weight, the sterol being selected from the group consisting of cholesterol, agnosterol, ergosterol, dehydrocholesterol, cholestanol, beta-sitosterol, zymosterol, lathosterol, hydroxycholesterol, dehydro-ergosterol, and ascosterol.

12. The composition according to claim 1, wherein the triglyceride is provided by the addition of a natural fatty substance including glycerine and a fatty acid selected from the group consisting of lauric, myristic, palmitic, stearic, arachidic, palmitolic, oleic, eleostearic, linoleic, linolenic, arachidonic, and ricinoleic acid.

13. The composition according to claim 1, wherein said amino-acid consists of amino-acids having different aliphatic chains R chosen from the group consisting of octyl, capryl, lauryl, myristyl, cetyl, stearyl, oleyl and linoleyl.

14. A disinfectant composition which comprises an aqueous solution having 0.6 to 2.5% by weight of alkyl-diethylene-triamino-acid acid, the alkyls of which contain $C_8$ to $C_{18}$ with about 80% of them containing $C_{12}$ and $C_{14}$ the solution having dispersed therein 2 to 10% by weight of sweet almond oil and containing 1,000 to 5,000 I.U. of vitamin A, 1 to 25 I.U. of vitamin E and 50 to 50,000 I.U. of vitamin D per 100 grams of composition, and having also dispersed therein an amount of lanoline capable of providing 0.02 to 0.5% by weight of sterols selected from the group consisting of cholesterol, agnosteol, ergosterol, dehydrocholesterol, cholestanol, beta-sitosterol, and ascosterol as well as 0.015 to 1.1% by weight of an alkanol having 8, 12, or 16 carbon atoms, the pH of the composition being adjusted to a value of 6.5 to 7.2.

15. An aqueous disinfectant composition, suitable for prolonged application to the skin without irritation and useful against bromidrosis, which comprises an aqueous solution of:
(a) 1 wt. % of dodicin,
(b) a vitamin component chosen from the group consisting of:
   400 I.U. (per 100 grams of composition) of Vitamin A, and
   1 I.U. (per 100 grams of composition) of Vitamin E, and
(c) 3 wt. % oleic triglyceride.

* * * * *